Figure 1:
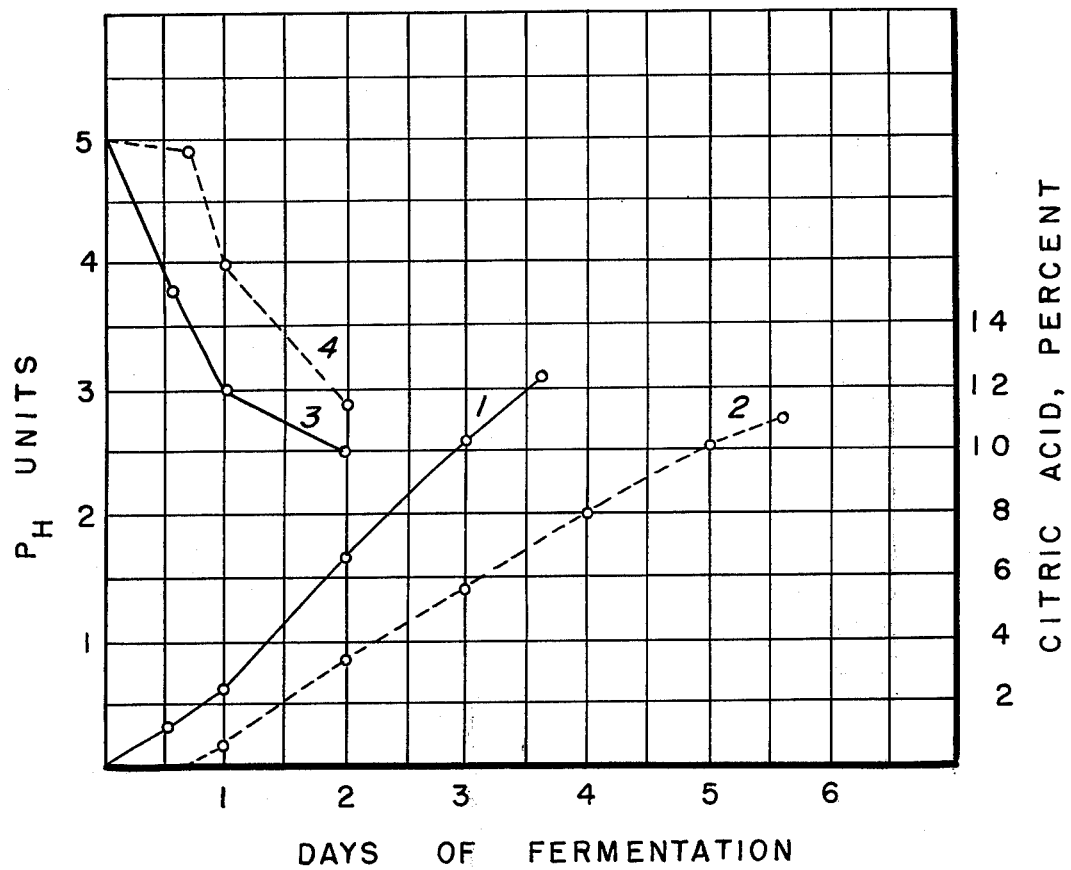

United States Patent [19]

Hustede et al.

[11] 3,940,315

[45] Feb. 24, 1976

[54] PRODUCTION OF CITRIC ACID BY SUBMERGED FERMENTATION

[75] Inventors: Helmut Hustede, Ladenburg (Neckar), Germany; Herman Rudy, deceased, late of Heidelberg, Germany; by Liselotte Rudy nee Ringelmann, heir; by Hans Rudy, heir, both of Heidelberg, Germany; by Barbara Sallewsky nee Rudy, heir, St. Hermas, Canada

[73] Assignee: Joh. A. Benckiser GmbH, Ludwigshafen (Rhine), Germany

[22] Filed: Nov. 2, 1971

[21] Appl. No.: 195,076

[52] U.S. Cl. .............................................. 195/36 R
[51] Int. Cl.² ........................................... C12D 1/04
[58] Field of Search ............................ 195/36 R, 37

[56] References Cited
UNITED STATES PATENTS
3,118,821  1/1964  Clark .................................... 195/36

OTHER PUBLICATIONS

Quadeer et al., Chemical Abstracts, Vol. 72, 77401 a, 1970.

*Primary Examiner*—Lionel M. Shapiro
*Attorney, Agent, or Firm*—Weiser, Stapler & Spivak

[57] ABSTRACT

The invention concerns the production of citric acid-producing mycelial pellets of a citric acid-producing microorganism by a selective treatment with ferrocyanide or ferricyanide ions. Known Asperigillus or Penicillium are well suited for the fermentation. The invention also concerns the production of citric acid with the pellets of the invention by submerged fermentation. The fermentation is remarkably more efficient than conventional methods, greater yields being obtained in a shorter time.

23 Claims, 1 Drawing Figure

PRODUCTION OF CITRIC ACID BY SUBMERGED FERMENTATION

The invention relates to the production of citric acid by aerobic submerged fermentation of a sugar-containing medium, particularly black-strap molasses or sugar beet molasses. In particular, the invention concerns a process for the production of citric acid by submerged fermentation which is carried out in the presence of ferrocyanide or ferricyanide ions which has been added to the fermentation at a specific time, by reference to the evolution and growth of the citric-acid microorganism.

A first important embodiment of the invention provides a method for preparing special citric acid-producing mycelial pellets by a selective treatment of spores of a citric acid-producing microorganism with ferrocyanide or ferricyanide ions, like potassium ferrocyanide. The method changes the morphology and biological metabolism of the microorganism to a microorganism pellet capable of producing citric acid in a most efficient manner. A second embodiment of the invention provides a remarkably efficient process for producing citric acid with such microorganism pellets.

FIG. 1 illustrates by two curves the rate of production of citric acid and by two other curves the accompanying drop of pH. comparing the method of the invention and the conventional method.

In general, as disclosed in the prior art, the methods for preparing citric acid by submerged fermentation proceed in two stages. In the first stage the inoculum of the microorganism is grown; in the second stage, the main fermentation stage, the actual fermentation of the medium to citric acid is carried out.

It is known from processes of the prior art that "mush" mycelium or pellet type mycelium such as is disclosed, for instance, in U.S. Pat. No. 2,910,409, may be produced in the fermentation to citric acid. The term mush-mycelium describes long, loosely branched and relatively thin hyphae in mat-like form. In contrast thereto, the term "pellet" is used to describe spherical-shaped mycelium aggregate which is composed of very short branched and comparatively thick hyphae. Often these have bulb-like extremities or they carry short-branched buds. Such pellets have been described adequately in the literature as for instance in U.S. Pat. No. 2,739,928 to Martin. Furthermore, Beligian patent No. 596,964 and Can. J. Microbiol., 1, 150–157 (1954) suggest various ways for growing such pellets. Other representative art method include U.S. Pat. Nos. 3,118,821 and 3,189,527 to Clark and Lockwood, respectively. In accordance with one known procedure, pellet formation was accomplished by using a highly diluted special nutrient solution, with special aeration effects. On the other hand, pellet formation was induced by means of specific additives such as the addition of potassium ferrocyanide from the time of inoculation with the spores. The disadvantages of such methods are that the resulting pellets undergo a longer period of adapation in the main fermentation after inoculation of the medium. Moreover, the pellet information ensues from mycelium aggregation, so that, for instance, many spores are necessary for the development of a single pellet.

It is therefore a general shortcoming of the known methods that the beginning of the fermentation to citric acid itself is preceded by a longer growth adaptation or acclimatization period during which essentially no citric acid is formed. As a result, there is a lag of 16 to 48 hours depending on the particular method until the start of the real fermentation to citric acid. During that time, the development of the fungi is exceptionally labile; it is only under certain conditions that the further development of an active mycelium can be insured, such as, for instance, through shock by means of an acid or by means of intensive aeration with pure oxygen or mixtures of oxygen and air.

It is evident from a study of the prior art that notwithstanding very numerous attempts and extensive research in this field, there is a serious need for an improved method for making citric acid. This acid has numerous uses in the pharmaceutical, food and sanitary fields such as in detergent compositions for household and other uses. The supply of the chemical falls short of world requirements.

A process has now been found which in accordance with the invention overcomes the difficult problems of the prior art. In accordance with the process of the invention, there are used in the main fermentation for the production of citric acid special pellets of *Aspergillus niger* or other suitable citric acid-producing microorganism, which have already been pre-activated or pre-treated in a separate pre-culturing method. In accordance with the invention, the pre-culturing method comprises activating by a treatment with cyanide ions a young inoculum of the microorganism during its highly intensive physiological development and labile phase, which takes place during the transition period from the spore-swelling stage to the beginning of the germination stage of the microorganism by means of an "aimed" or selective shock of the enzyme system of the microorganism. The method comprises treating, at the particular time defined, the inoculum of the microorganism with potassium ferrocyanide or other equivalent ferri- or ferrocyanide salt with a selected amount such as of about 0.5 to 3 grams, particularly 1.5 to 2 grams of potassium ferrocyanide per liter of fermentation medium. This treatment apparently causes a selective shock of the microorganism's enzyme system. In accordance with this invention, it has been found that by timing the addition of the cyanide ion, like potassium ferrocyanide selectively so as to take place during this intensive and labile growth stage, it has been possible to cause a remarkably high development of acid-stable pellets which have a remarkable propensity for producing citric acid.

As disclosed above, the selective shock of the microorganism enzyme system is carried out very advantageously with a ferro-or ferricyanide ion. It is contemplated, in accordance with the invention, that the enzyme system of the citric acid-producing microorganism be selectively affected, and for this purpose other inorganic or organic specific compounds can be used. What is determinative in accordance with the finding of the invention is the timing of the addition of the specific compound to take place, as described above.

In the invention provided herewith the particular addition of ferrocyanide or ferricyanide ions takes place during and relative to particular stage of development of the citric-acid producing microorganism, namely that period starting with the spore-swelling stage up to the spore-germinating stage of the microorganism in a suitable growth medium. The condition of the medium that is, the presence or absence of ferro- or ferricyanide ions prior to or at the spore-swelling stage of the microorganism (i.e. at the time of addition of the cyanide ions) is thus of secondary importance. It is the presence of these ions at the time specified which is, in accordance with the invention, the determinative aspect thereof. Hence, the medium in which the microorganism spores are present can contain prior to or up to the moment of addition of cyanide ion — hence prior to or up to the spore-swelling stage — ferro- or ferricyanide ions in varying amount. These cyanide ions will bind an equivalent amount of complexable substances which are present in the medium. However, the amount of ferro- or ferricyanide ion which is present prior to or up to the time of treatment should not exceed that amount which is capable of complexing most or all of the complexable substances present in the medium, which may include complexable salts. Hence, there should be no free or uncomplexed ferro- or ferricyanide ion present at the time of treatment with the ferro- or ferricyanide in accordance with the invention. If such an amount of free or excess ferro- or ferricyanide were present, it would deter from obtaining maximum benefits of the invention, namely of the selected shock effect attained by the addition of the ferro- or ferricyanide at the time specified during the stage of development of the microorganism, as described above.

In accordance with the invention, there is used, at the time specified, a ferro- or ferricyanide ion as a suitable salt, preferably a water-soluble salt such as an alkali metal salt. The salt should be capable of liberating ferro- or ferricyanide ions under the process condition. At the present potassium ferrocyanide is preferred. The amount of salt to be used in the practice of the invention are based on potassium ferrocyanide. For ready conversion to ferricyanide ion, the amounts given for the potassium salt are divided by two. The amount of ferricyanide ions to be used is therefore 0.25 to 1.5, preferably 0.75 to 1.0 gram per liter. Whenever the term ferrocyanide is used it is intended to include ferricyanide too.

It has been observed that if the timing of the addition of ferrocyanide ions is not observed, the process of the invention does not proceed as intended herewith. If the potassium ferrocyanide is added from the beginning, i.e., at the time of or prior to inoculation, as is known, there already occurs during the vegetative stage a certain amount of adaptation, so that no shock effect with the ferrocyanide takes place. As a result, a relatively longer adaptation period takes place during the main fermentation. It is an advantage of the invention that such adaptation is substantially eliminated. Furthermore, if the enzyme shock is carried out at a later time than provided herein, the development of the mycelium has already proceeded so far that a specially activated pellet cannot be produced. It is, therefore, an important aspect of the invention that the timing of the addition of the potassium ferrocyanide during the growth of the inoculum be carried out at the time specified in order that the special pellet be produced which is capable of the remarkably efficient formation of citric acid in the main fermentation.

In practice, the spores of the inoculum of the citric acid-producing microorganism reach the stage of intensive physiological development approximately 7 to 10 hours after inoculation. The desired morphological development stage of the spores is determined by periodic macro- and microscopic observations of the culture on samples removed from the medium. Depending on the particular conditions selected, the stage of intensive physiological development of the spores may be controlled to be reached earlier or later. When the spores show evidence of swelling and prior to germination, they are subjected to a ferrocyanide treatment, like with potassium ferrocyanide. The addition of the potassium ferrocyanide insures the formation of citric acid-forming activated pellet of mycelium and essentially eliminates the adaptation period in the subsequent fermentation of the sugar. Moreover, the inoculum so treated develops a pellet from at least 90% of the spores present, generally from each labile inoculated spore. Accordingly, the pre-fermentation medium only needs to be inoculated with the number of labile spores that correspond to the number of pellets necessary for the main fermentation. In contrast, in accordance with known methods, the growth of pellet mycelium requires 500 to 600 spores to develop each pellet, so that the requirement for spores by far exceeded that of the present invention.

In accordance with the method of the invention, it is advantageous to carry out the preparation of the activated pellet in about a period of 20 to 28 hours. At that time, the individual activated pellets reach a diameter of about 0.15 to about 0.2 mm. and the pH of the pre-fermentation medium drops by about 0.5 to 1 pH unit from an initial pH range of about 4.3 to about 6.2, which is substantially similar to that of the fermentation medium. Thus the pellet is adequately activated when a distinct pH drop is noted, thereby evidencing the initiation of the acid-producing stage and the termination of the spore-activating stage. Conveniently, this later stage can be considered terminated when the pH drops within the range of 4.0 to 4.5.

In accordance with this first embodiment of the invention, there are obtained specially activated pellets which are remarkable in their ability to produce citric acid efficiently.

In the second important embodiment of the invention, the resulting activated pellets are used as inoculum for the main fermentation to citric acid, for instance, of a fermentation of a black-strap molasses having a suitable sugar concentration as, for instance, a 15% concentration. The size of inoculum can be varied as desired, for instance from 2 to 20%, or more, commonly 8 to 12% of inoculum per volume of fermentation medium may be used. The inoculum of pellets remains uninterruptedly in the acid-forming stage so that already after 24 hours a pH drop of about 1.5 to 2 pH units takes place.

It is, therefore, a characteristic of the fermentation of the invention that citric acid is actively produced essentially from the start — i.e. from time of inoculation of the main fermentation medium to the end of the fermentation at substantially the same rate. Thus in the present process, the initial rate of formation of citric acid exceeds by far that of convential methods, as is evidenced, for instance, by its rapid initial pH drop. In accordance with known methods using a conventional inoculum, such a pH drop does not take place because of the necessary adaptation period of the microorganism. Accordingly, in prior art method it had been necessary to adjust the pH in the main fermentation by the addition of acid. In accordance with the invention, the necessity of adding acid is completely eliminated and the main fermentation is terminated in 3 to 4 days with a yield of 70 to 100% based on the initial amount of sugar present. In a further aspect of the process of fermentation of the invention it is desirable to add potassium ferrocyanide to a minimum concentration of at least 0.2 gram per liter. In the main fermentation the amount of potassium ferrocyanide may range from about 0.5 to 3 gram, more commonly from 0.8 to 1.5 gram per liter of medium.

The invention provides another further advantage in that the pre-culturing of the inoculum, as well as the fermentation phase itself are aerated only with air. No supplementary aeration with oxygen is needed. The aeration requirement of the invention can be decreased to about 0.2 volume per volume of medium per minute without adversely influencing the fermentation. Generally an upper range of 0.5 to 0.4 is quite satisfactory. The reason for the low air requirement of the process of this invention appears to be the absence of by-products in the fermentation phases of the activated mycelium, which would increase the viscosity of the medium, such as occurs by the use of other forms of conventional inoculum which have to undergo the necessary adaptation period. Furthermore, foam formation remains substantially constant during the entire course of the fermentation; the need for defoamers is not increased. Another advantage is that the danger of contamination by other microorganisms is practically excluded because the activated pellets essentially immediately form citric acid intensively in the main fermentation, as is evidenced by a strong pH drop such as of about 1.5 to 2.0 units in about 28 hours, thus creating a medium unfavorable for contamination by other microorganisms.

The citric acid-producing pellets used in the method of the invention are identifiable morphologically by known microbiological and mycological techniques. The term "specially activated pellet" used herein and the pellet produced by treating the spores at the selective time specified defines a pellet whose metabolism has been so altered that it produces citric acid essentially uninterruptedly from the time of the formation of the pellet without undergoing the typical adaptation lag which precedes the active citric acid forming stage of the conventional pellets. This unique property of the pellet of the invention is also observable from curves plotting the formation of citric acid from the time of the pellet formation to the end of the utilization of the sugar. For instance, a typical curve plotting acid formation against days of fermentation shows during its first fifth, or first quarter after the first day, a slope which is substantially the same as that for the remainder of the fermentation. These special pellets are thus unique in their absence of an adaptation lag which is the characteristic of the conventional pellet and in their ability to produce citric acid by fermentation immediately subsequently to the activation period. Thus, in contrast to the conventional pellets, the specially activated pellet of the invention produces citric acid after inoculation of the fermentation medium at a rate substantially equivalent to that which the conventional pellet produces after such pellet has passed its adaptation lag.

In FIG. 1 which illustrates the rates of conversion to citric acid in accordance with the invention and that of a conventional method, curve 1 represents the production of citric acid as described in Example 2 and curve 2 that of Example 4, the latter being the conventional method.

It is apparent from FIG. 1 with respect to curves 1 and 2, the citric acid production curves, that the rate of citric acid production is remarkably faster in accordance with the method of the invention. It is noteworthy that in the method of the invention, the fermentation is essentially terminated, that is, there is no more convertible sugar present, generally in about 3 days; in contrast, in conventional methods, not more than about 50%, generally from about 30% to about 50% of the convertible sugar is consumed during that time. In 3 days, the method of the invention produces about twice as much citric acid as the conventional method. See FIG. 1. 5.5 v. 10.5 production of citric acid, respectively measured as percent citric acid. In FIG. 1 Curves 3 and 4 represent the pH curves corresponding to the fermentation represented by curves 1 and 2, respectively. Curve 3 shows the lowering of the pH in accordance with the invention, immediately following inoculation of the medium, without any adaptation period. In contrast, curve 4 shows no drop of pH of the medium during the initial period following inoculation, hence there is an adaptation lag before citric acid production can start. From FIG. 1 it is evident that in accordance with the invention, citric acid is produced more efficiently during any given time period in accordance with the method of the invention.

In the process of the invention, there may be used any of the citric acid producing microorganisms such as the genera Aspergillus, Penicillium or Mucor. Examples of useful species of these genera are *A. niger*, *A. wentii*, *A. clavatus*, *P. citrinum*, *Mucor piriformis* and *Trichoderma viride* (ATCC No. 1323). The species which has been found most useful is *A. niger*. Among these such strains at ATCC 10577, ATCC 1015 or Wisconsin 72-4, also named N.R.C.A.-1-233 (National Research Council Publication No. 2359), and mutants thereof are quite suitable. Other suitable microorganisms are disclosed in the scientific literature. Suitable microorganisms which produce citric acid are on deposit in recognized depositories like the American Type Culture Collection, Washington, D.C. (ATCC), Headquarters Quartermaster Research and Development Command, Quartermaster Research and Development Center, U.S. Army (QM), Northern Regional Research Laboratory of the Department of Agriculture, Peoria (NRRI), Nagoa Institute, Tokyo (NI), Institute of Fermentation, Osaka (IFO), National Hygienic Laboratory, Tokyo (NHL) and Kyowa Hakko Kogyo Co., Ltd. (Kyowa).

The fermentation medium may contain any carbohydrate source which can be converted to citric acid by the microorganism, like a sugar from conventional crude sugar sources, as sugar beet, sugar cane molasses or citrus molasses or other carbohydrates and suitable nutrient salts such as, for instances, phosphates, nitrates, and so in suitable amounts and conditions of growth, as is known from the prior art such as from U.S. Pat. Nos. 2,739,923; 2,970,084; 2,674,561; 2,883,329; 2,910,409; 2,492,673; 2,492,667; 2,400,143; 2,394,031; Belgian patent No. 596,964 and others Determination of ferrocyanide ions is performed in accordance with the method of J. R. Marier and D.S. Clark, the Analyst, J. Soc. Anal. Chem. 85 No. 1013, pp. 574–579 (1960). The accuracy of the method is +3 V/ml. The yield of citric acid is determined as percent citric acit (wt.vol. of medium) or percent conversion of available sugar. (wt./wt.)

The following working examples are provided as an illustration of the preferred embodiments of the invention but are not to be construed as a limitation thereof.

EXAMPLE 1

In a suitable fermentation vessel there are fed 320 liters of fermentation medium of black-strap molasses. The molasses are diluted with tap water to an approximate concentration of 15% of sugar. There is then added to the medium 80 g. of ammonium dihydrogen monophosphate. The pH is adjusted to 5.0 and the medium then sterlized. Aeration provided by an air sparger feeds from the beginning a total of about 6 to 8 cubic meter per hour of air into the medium. The air is distributed by stirring with a stirrer rotating at the speed of 300 r.p.m.

The medium is inoculated at 32°C. with $4 \times 10^{10}$ spores of *Aspergillus niger*. Eight hours after the inoculation there are added 480 g. of potassium ferrocyanide. Within a total of 18 to 19 hours, there is formed from each spore a mycelium of a length of about 0.4 to 0.7 mm. Each one of the extremities of the mycelium is club-like thickened and has a branched cauliflower-like appearance. This structure develops into pellets which have an approximate diameter of about 0.2 mm in the next four hours and is accompanied by a sharp pH drop. When the pH value drops to about 4.3, enough pellets in medium are collected to serve as inoculum.

EXAMPLE 2

A fermenter tank of a capacity of 3 cubic meter is charged with a fermentation medium of the same composition and sugar content as was described as example 1. Its pH is likewise adjusted to about 5.0 and then the medium 2.4 cubic meters, is sterilized in a similar manner. After cooling the fermentation medium to a temperature range of about 28°–32°C. there are added 3000 g. of potassium ferrocyanide. Prior to inoculation, the medium is aerated by a sparger so as to feed 0.2 volume of air per volume of medium per minute in an amount equivalent to about 35–40 cubic meter per hour. Stirring by means of an appropriate stirrer rotating at a rate of 100 r.p.m. distributes the air throughout the medium. An inoculant of pellets prepared as in example 1 is used to inoculate the medium. After the inoculation, samples are removed to determine the pH which has been lowered as a result of the inoculation. After three further hours of uninterrupted fermentation by the activated pellet mycelium, the pH has already dropped by 0.1 to 0.2 units. After about 18 hours of fermentation there are added 750 g. of ammonium nitrate and the potassium ferrocyanide concentration is determined. When it is found to fall to a concentration below 0.3 g. per liter, it is raised again to a concentration of at least 0.4 g. per liter by addition of potassium ferrocyanide. In this matter the concentration of potassium ferrocyanide does not fall below 0.2 g. per liter throughout the entire fermentation. After 48 hours of fermentation there are again added 750 g. of ammonium nitrate.

After three days of fermentation the pH value of the fermentation medium has dropped to a pH of 2.45 and the citric acid concentration is 10.5%. This corresponds to a yield of 70% based on the initial amount of sugar present. After a further 15 hours, the fermentation is terminated. The citric acid concentration is 12.3% corresponding to a yield of 82% based on the initial amount of sugar present.

EXAMPLE 3

Example 2 is repeated increasing the sugar concentration to 20%. An equally satisfactory efficient fermentation to citric acid was obtained.

EXAMPLE 4

In a comparative experiment to that of Example 1, when the potassium ferrocyanide was added after sterilization and before inoculation, only a 72% yield of citric acid was obtained after a fermentation at least 2 days longer.

EXAMPLE 5

When the procedure of Example 1 is repeated with *A. venti*, pellet formation results in a similar manner.

EXAMPLE 6

When the pellets of *A. venti*, of Example 5 are used in a fermentation as in Example 2, citric acid is likewise formed.

EXAMPLE 7

Likewise the use of *P. citrium* under the conditions of Example 1 yields pellets useful in citric acid formation.

EXAMPLE 8

When the pellets of *P. citrium* are used in a fermentation, under condition similar to those of Example 2, good yields of citric acid are obtainable.

EXAMPLE 9

In a fermentation vessel there is fed 320 liters of fermentation medium of beet molasses which have been diluted with tap water to a concentration of approximately 15% sugar. To this solution there is added 80 g. of ammonium dihydrogen phosphate; the starting pH is 5.5. The medium is sterilized thereafter by heating 35 minutes at 100°C. After cooling, the medium is aerated with about 6 to 8 m³ air with stirring at rate of 300 r.p.m. Thereafter, the medium is inoculated with about $4 \times 10^{10}$ of spores of *Aspergillus niger* and the medium is maintained at a temperature of 32°C. After about 6 hours after the inoculation, there are added about 480 g. potassium ferrocyanide. Under these conditions there are formed from each individual spore a mycellium of a length of about 0.04 to 0.07 mm, which at its both ends is swollen and branched in a cauliflower-like fashion. In about 3 or 4 hours each short hyphae develops and transforms into a pellet of a diameter of approximately 0.2 mm. Concurrently, there takes place an intensive and active acid formation and the pH drops to about 4.6. The preparation of the inoculum is thus terminated.

The fermentation itself is carried out in a fermentation tank of 3000 liters in which there is contained sugar beet molasses which has been diluted with tap water to a sugar concentration of about 15%. The pH buffer capacity of such beet molasses being very high, it is desirable to lower it by lowering the pH to about 5.5 with a suitable and, like sulfuric acid. The pH of the molasses solution is therefore brought down to about 5.5 with sulfuric acid. The sterilization of the medium 2.4 cubic meters, is then carried out following the procedure shown above by repeatedly heating to 100°C. After cooling to about 28° to 32°C. there are added 2400 g. of potassium ferrocyanide. The medium so prepared is then aerated with about 40 m³ of air per hour. The air is well distributed within the medium by stirring the medium at a rate of 100 r.p.m.

The aerated medium is inoculated with the pellets which have been prepared as described above. With the initiation of the acid formation the pH drops to about 5.0 in 6 to 10 hours. The intensive citric acid fermentation is accompanied with an intensive mycellium growth. The temperature of fermentation is adjusted and maintained at 29°C. In order to interrupt the intensive growth stage of the mycellium there is added to the medium within one hour, sulfuric acid in such an amount that the pH value drops to about 3.0 to 2.9. After about 20 hours of fermentation there are added 600 g. of ammonium dihydrogen phosphate. Whenever the concentration of ferrocynanide ions is or drops below 0.5 g. per liter, there are added additional amounts of potassium ferrocyanide in order to raise the concentration to about 0.6 g. per liter. The concentration of potassium ferrocyanide is maintained till the end of the concentration to a minimum of 0.4 g. per liter.

After about five days the fermentation is terminated. The fermentation medium contains or has a concentration of citric acid of about 11.5% which corresponds to a yield of about 77% calculated on the amount of sugar initially present.

EXAMPLE 10

In the fermentation tank of the capacity of 3 cubic meters there is fed a mixture of black-strap molasses and concentrated solution of sugar (from crystallized sugar) the fermentation liquor, 2.4 cubic meters, being diluted with tap water to a total sugar concentration of about 15%. The amount and the proportion of molasses and sugar have been so selected that half of the total sugar due to the black-strap molasses while the other half amount of sugar is from crystallized sugar from the sugar solution. After the pH has been adjusted to initial value of 5.0, the fermentation medium is sterilized in the manner shown above and then cooled to about 28° to 32°C.

There are added therein 1,400 g. of potassium ferrocyanide. The pre-culturing of the inoculum, the inoculation and the subsequent fermentation are carried out as shown in Examples 1 and 2. It is advisable in this fermentation in which sugar has been added, that the fermentation medium be aerated with a somewhat larger amount of nitrogen. After about 3 to 4 hours after the inoculation with pellets of the *Aspergillus niger* which is obtained as shown in Example 1, there is added 600 g. of ammonium nitrate and 800 g. mono ammonium phosphate.

The fermentation itself is terminated in about 4 days. The concentration of citric acid in the fermentation medium is about 13% which corresponds to about 86% of conversion on the basis of the original sugar.

EXAMPLE 11

The method of Example 10 is repeated with sodium ferrocyanide. Active pellets similar to those above described are formed and then used in the fermentation of black-strap molasses to citric acid, in the manner described above.

EXAMPLE 12

The method of examples 1 and 2 are repeated using potassium ferricyanide with equally satisfactory results.

EXAMPLE 13

When the procedure of Examples 1 and 2 is repeated with the following:
a. *A. wentii*
b. *P. citrinum*
c. *A. clavatus* like results are obtained. Other species of *A. niger* yield pellets effective to give the desired citric acid.

We claim:
1. The method of preparing mycelial pellets of a citric acid-producing miroorganism for the manufacture of citric acid in a carbohydrate-containing growth medium which comprises treating spores of a citric acid-producing microorganism in the carbohydrate-containing growth medium free of unbound cyanide ions by adding ferro- or ferri-cyanide ions during the physiologically intensive development period which takes place during the transition period ranging from the spore-swelling stage to the spore-germination stage, and forming mycelial pellets therefrom.

2. The method of claim 1 wherein the microorganism is an Aspergillus.

3. The method of claim 1 wherein the medium is a molasses-containing medium.

4. The method of claim 2 wherein the Aspergillus is *A. niger*.

5. The process of claim 1 wherein the cyanide ions are provided by potassium ferrocyanide.

6. The method of claim 5 wherein the potassium ferrocyanide is added to the spores in the medium after about 7 hours after inoculation and not later than 10 hours thereafter.

7. The process of claim 5 wherein a mycellial pellet is formed from essentially each one of the spores.

8. The method of claim 1 wherein the mycelial pellets which are formed are characterized by a pH development curve essentially free of a lag period.

9. The method of claim 1 in which the pH drops by about 0.5 to about 1.0 unit after the cyanide treatment.

10. The method of claim 5 in which the potassium ferrocyanide is used in an amount of about 0.5 to 3.0 gram per liter.

11. The process of claim 1 wherein the microorganism is a Penicillium.

12. The process of claim 11 wherein the Penicillium is *P. citrinum*.

13. The process of claim 2 wherein the microorganism is *A. wentii*.

14. The process of producing citric acid by submerged aerobic fermentation which comprises
inoculating a carbohydrate-containing medium with a mycelial pellet of a citric acid-producing microorganism, said pellet having been produced by having treated the spores of a citric acid-producing microorganism in a carbohydrate-containing medium free of unbound cyanide ions with ferro- or ferri-cyanide ions during the physiologically intensive development period which takes place during the transition period ranging from spore-swelling stage to the spore-germination stage, and characterized by its substantial absence of an adaptation lag in the fermentation as evidenced by its pH curve and
producing citric acid at a substantially constant rate from the time of the inoculation of the fermentation medium with the pellet throughout, and to the end of the fermentation.

15. The process of claim 14 wherein the medium is a molasses-containing medium.

16. The process of claim 14 of producing citric acid by submerged aerobic fermentation which comprises
inoculating a molasses-containing medium with a mycelial pellet of Aspergillus, said pellet being produced by having treated the spores of a citric acid-producing microorganism in a carbohydrate-containing medium free of unbound cyanide ions with ferro- or ferri-cyanide ions during the physiologically intensive development period which takes place during the transition period ranging from the spore-swelling stage to the spore-germination stage, and characterized by the substantial absence of an adaptation lag in the fermentation as evidenced by its pH curve, and producing citric acid at a substantially constant rate from the time of the inoculation of the fermentation medium with the pellet throughout, and to the end of the fermentation.

17. The process of claim 16 wherein a pH drop of at least about 2.0 units in 24 hours after inoculation takes place.

18. The process of claim 16 in which there occurs a drop of at least about 1.5 units.

19. The process of claim 14 in which the concentration of ferro- or ferricyanide ions is maintained at a minimum of about 0.2 gram per liter during the fermentation.

20. The process of claim 14 in which the aeration provided does not exceed about 0.4 volume of medium per minute.

21. The process of claim 13 wherein the Aspergillus is *A. niger*.

22. The method of preparing mycelial pellets of a citric acid-producing microorganism for the manufacture of citric acid in a carbohydrate-containing growth medium which comprises treating spores of a citric acid-producing microorganism in the carbohydrate-containing growth medium free of unbound cyanide ions by adding ferro- or ferri-cyanide ions in an amount of 0.25 to 1.5 g per liter of medium during the physiologically intensive development period which takes place during the transition period ranging from the spore-swelling stage to the spore-germination stage, and forming mycelial pellets therefrom.

23. The method of claim 22 in which the amount of cyanide ions range from about 0.75 to 1.0 g per liter.

* * * * *